United States Patent [19]

Masuda et al.

[11] Patent Number: 5,223,143
[45] Date of Patent: Jun. 29, 1993

[54] PROCESS FOR FRACTIONAL SEPARATION OF A PLURALITY OF COMPONENTS FROM THE MIXTURE THEREOF

[75] Inventors: Takayuki Masuda, Tokyo; Tohru Sonobe, Saitama; Kikuzo Kaneko, Tokyo; Fumihiko Matsuda, Saitama, all of Japan

[73] Assignee: Japan Organo Co., Ltd., Tokyo, Japan

[21] Appl. No.: 897,795

[22] Filed: Jun. 12, 1992

[30] Foreign Application Priority Data

Jun. 12, 1991 [JP] Japan .................................. 3-140336

[51] Int. Cl.⁵ .............................................. B01D 15/08
[52] U.S. Cl. ................................ 210/659; 210/198.2; 127/46.1; 127/46.2
[58] Field of Search ............... 127/30, 46.1, 46.2, 127/46.3, 55; 210/635, 656, 659, 198.2

[56] References Cited

U.S. PATENT DOCUMENTS

| | | | |
|---|---|---|---|
| 4,498,991 | 2/1985 | Oroskar | 210/659 |
| 4,970,002 | 11/1990 | Ando | 210/659 |
| 4,990,259 | 2/1991 | Kearney | 210/659 |
| 5,064,539 | 11/1991 | Tanimura | 210/198.2 |
| 5,093,004 | 3/1992 | Hotier | 210/659 |
| 5,102,553 | 4/1992 | Kearney | 210/659 |
| 5,114,590 | 5/1992 | Hotier | 210/659 |
| 5,122,275 | 6/1992 | Rasche | 210/659 |
| 5,126,055 | 6/1992 | Yamashita | 210/659 |

FOREIGN PATENT DOCUMENTS

| | | | |
|---|---|---|---|
| 1418503 | 12/1975 | United Kingdom | 210/657 |
| 2240053 | 7/1991 | United Kingdom | 210/659 |

*Primary Examiner*—Ernest G. Therkorn
*Attorney, Agent, or Firm*—Wenderoth, Lind & Ponack

[57] ABSTRACT

There is provided a process for efficient chromatographic separation of a plurality of components from a fluid feed containing the same, which process comprises repeating a cycle comprising the step (1) of substantially shutting off the internal fluid circulation at a position of endless, or continuous, circulatory system and withdrawing a fraction enriched with a component having a strong affinity for an adsorbent upstream of the shut-off position while feeding the fluid feed downstream of the shut-off position, and the step (2) of withdrawing a plurality of fractions enriched with the remaining components while feeding a fluid desorbent and circulating the internal fluid.

8 Claims, 5 Drawing Sheets

PROCESS FOR FRACTIONAL SEPARATION OF A PLURALITY OF COMPONENTS FROM THE MIXTURE THEREOF

BACKGROUND OF THE INVENTION

1. Field of the Invention

The present invention relates to a process for separating, or isolating, at least two fractions each enriched with a component from a fluid containing a plurality of useful components, and particularly relates to a process for separating a plurality of components contained in a gas or liquid containing at least two or three components according to a chromatographic procedure.

2. Prior Art

Processes for separating a Plurality of components according to a chromatographic procedure (hereinafter referred to as a chromatographic separation process have heretofore been widely utilized on an industrial scale.

For example, many packed bed units 1 to 8, as shown in FIG. 4, packed with a solid adsorbent are connected in a series of circulation to establish a chromatographic system. The so-called simulated moving bed process involves feeding of a fluid feed f, a liquid in particular, to the above-mentioned system from the outside of the system, feeding of an eluant D as the desorbing fluid to the system from the outside of the system, withdrawal of fractioned components A and B from the system to the outside of the system, circulation of an internal liquid by means of a circulation pump, switching of valves $1a$ to $8a$, $1b$ to $8b$, $1d$ to $8d$ and $1e$ to $8e$ to simulate a moving bed to thereby continuously separate the components A and B. This simulated moving bed process is known as being excellent in separation performance and high in productivity to make the process as well as equipment therefor advantageous.

The simulated moving bed process as briefly described above is required to have feeding inlets for a fluid feed and feeding inlets for a desorbing fluid (hereinafter referred to as a fluid desorbent ) between adjacent packed bed units, and withdrawal outlets for withdrawing fractions of components to be withdrawn. Accordingly, not only simulation of a moving bed without actual movement of an adsorbent is difficult to understand in an aspect of principle, but also adoption of a complicated structure of whole equipment as described above is difficult to avoid in another aspect. Thus, as compared with equipment for a batch operation, which equipment can realize separation of components from a mixture thereof by a relatively simple operation, continuously operable equipment requires a high degree of control technology. Accordingly, such continuously operable equipment is known to bear an onus, or burden, of an overall equipment cost in aspects of both hardware and software.

Furthermore, a simulated moving bed mode of processes has heretofore been, in general, used to fractionate components contained in a gas or liquid into two fractions. Thus, it has heretofore been considered difficult to fractionate a fluid containing at least three components into at least three fractions.

The inventors of the present invention have already proposed a method capable of separating at least three components without spoiling the excellent separability performance of the simulated moving bed mode by improving on the conventional technology of the simulated moving bed, which has heretofore been considered as being aimed at two, or twin, component systems as an object of separation.

Specifically, Japanese Patent Application No. 402,826/1990, which was proposed by the inventors of the present invention, discloses a process for fractional separation of a fluid mixture comprising a number of components into three or more components, which process is carried out in a system wherein a number of bed units packed with an adsorbent are linked with each other in endless, or continuous, series in such a way as to form a circulatory channel capable of circulation and shutoff, and wherein a fluid feed, or mixture, comprising three or more components having mutually different affinities for the adsorbent is flowed through said number of the packed bed units to form adsorption zones of the respective components separated from each other in the serial order of the weak to strong affinities thereof for the adsorbent; and which process comprises repeating a cycle comprising the step (1) of shutting off fluid circulation of said system at the shutoff position and feeding the fresh fluid feed into the system at a position downstream of the shutoff position while withdrawing from the system a fraction enriched with a component having an intermediate affinity for the adsorbent (predetermined component) selected from components present in adsorption zones located upstream of the shut-off position; and the step (2) of separately withdrawing enriched fractions of the respective components from the adsorption zones from which the predetermined component has not been withdrawn in the step (1) by feeding a fluid desorbent into the system from the upstream side of the adsorption zones with sequentially shifting the position of feeding the fluid desorbent and the positions of withdrawing enriched fractions, corresponding to the migration of the respective adsorption zones, in the downstream direction of circulation, while circulating the internal fluid throughout the system and feeding no fresh fluid feed into the system.

By the way, one characteristic of the above-proposed process is having the step of feeding the fluid feed while shutting off at least one position of the circulation system. The authors of the present invention have further found out that utilization of this characteristic step enables the following multi-component system separation operation.

Specifically, (1) the utilization of the step of feeding the fluid feed while shutting off fluid circulation at the shut-off position enables a fluid feed containing two components as an object to be subjected to the prior art simulated moving bed procedure to be more effectively fractioned into the respective fractions; and (2) in the step (2) of the above-proposed prior art process, the position from which the fluid desorbent is fed upstream of the adsorption zone enriched with a predetermined component while circulating the internal fluid by means of a pump or the like, the position from which the fraction enriched with the component having a strong affinity for the adsorbent is withdrawn, and the position from which the fraction enriched with the component having a weak affinity for the adsorbent is withdrawn, must be shifted in step with the migration of the adsorption zones of the respective components while sequentially shifting downstream the feeding inlet of the first-mentioned position and withdrawal outlets of the second- and third-mentioned postions, whereby sequence control as well as the structure of equipment tends to be complicated. Thus, a further improvement is demanded in simplification of the sequence control as well as the structure of equipment.

In view of the above, the present invention has been completed. Accordingly, an object of the present invention is to provide a novel process and equipment therefor which enable a mixture containing two or more components, two components in particular, to be effectively fractioned into fractions enriched with the respective components.

Another object of the present invention is to provide a process according to which separation, or fractionation, of three or more fractions, which has heretofore been impossible using the prior art twin-component simulated moving bed equipment, can be carried out using by far simpler simulated moving bed equipment than the prior art simulated moving bed equipment.

SUMMARY OF THE INVENTION

In order to attain the above-mentioned objects, the inventors of the present invention have completed the process of the present invention for separation of a plurality of components from the mixture thereof.

Specifically, in accordance with one aspect of the present invention, there is provided a process for effectively separating, or fractioning or isolating, two components from the mixture thereof in a system comprising a group of a few or more bed units packed with an adsorbent and connected with each other to form an endless, or continuous, series of a circulatory fluid channel in which system a state that a fluid, a liquid in particular, is flowed into the channel or to the outside of the channel while continuously circulating the internal fluid, can be changed into or from a state that the fluid is flowed into the channel or to the outside of the channel while substantially shutting off the internal fluid circulation at at least one position, and in which system a fluid feed containing two components having respective mutually different affinities for the above-mentioned adsorbent is flowed through the above-mentioned group of packed bed units to separately form an adsorption zone enriched with a component having a weak affinity for the adsorbent and an adsorption zone enriched with a component having a strong affinity for the adsorbent: which process comprises repeating a cycle of the step (1) of substantially shutting off the internal fluid circulation at least at a position immediately upstream of the packed bed unit where the components having the weak and intermediate or strong affinity for the adsorbent coexist, and withdrawing a fraction enriched with the component having a strong affinity for the adsorbent while feeding the fluid feed from the top, or upstream side, of the packed bed unit immediately downstream of the shut-off position or the second packed bed unit downstream thereof;

and the step (2) of withdrawing a fraction enriched with the component having the weak affinity for the adsorbent and remaining in the system after the step (1) above and sequentially shifting, in step with the migration of the adsorption zones downstream of the system, the position of feeding a fluid desorbent into the system and the position of withdrawing the fraction enriched with the component having the weak affinity for the adsorbent while circulatorily flowing the internal fluid without feeding the fluid feed but simultaneously feeding the fluid desorbent into the system.

Additionally stated, following the above-mentioned step (2) can be taken the step (3) of continuing withdrawing the fraction enriched with the component having the weak affinity for the adsorbent from the end of the packed bed unit containing said fraction and at the same time withdrawing the fraction enriched with the component having the strong affinity for the adsorbent from the end of the packed bed unit containing said fraction while circulating the internal fluid and feeding the fluid desorbent into the system. In this case as well, the position of feeding the above-mentioned fluid desorbent and the positions of withdrawing the respective fractions are sequentially shifted downstream of the system in step with the migration of the adsorption zones.

The authors of the present invention have also completed the following processes [1] and [2] of the present invention for the separation, or isolation or fractionation, of three or more components from the mixture thereof.

Specifically,

[1] in accordance with another aspect of the present invention, there is provided a process for effectively separating, or fractioning or isolating, a plurality of components from the mixture thereof in a system comprising a group of a few or more bed units packed with an adsorbent and connected with each other to form an endless, or continuous, series of a circulatory fluid channel in which system a state that a fluid, a liquid in particular, is flowed into the channel or to the outside of the channel while continuously circulating the internal fluid, can be changed into or from a state that the fluid is flowed into the channel or to the outside of the channel while substantially shutting off the internal fluid circulation at at least one position, and in which system a fluid feed having three or more components having respective mutually different affinities for the above-mentioned adsorbent is flowed through the above-mentioned group of packed bed units to separately form an adsorption zone enriched with a component having a weak affinity for the adsorbent, an adsorption zone enriched with a component having a strong affinity for the adsorbent, and at least one adsorption zone enriched with a component having an intermediate affinity for the adsorbent in the order of the strengths of affinity: which process comprises repeating a cycle comprising the step (1) of substantially shutting off the internal fluid circulation at a position immediately upstream of the packed bed unit where the components having the weak and intermediate or strong affinity for the adsorbent coexist, and withdrawing a fraction enriched with the component having the intermediate affinity for the adsorbent and subsequently withdrawing, from the same position as the foregoing fraction of the intermediate affinity, a fraction enriched with the component having the strong affinity for the adsorbent while feeding the fluid feed from top, or upstream side, of the packed bed unit immediately downstream of the shut-off position or the second packed bed unit downstream thereof; and the step (2) of withdrawing the fraction enriched with the component having the weak affinity for the adsorbent and remaining after the step (1) and sequentially shifting, in step with the migration of the adsorption zones downstream of the system, the position of feeding the fluid desorbent into the system and the position of withdrawing the fraction enriched with the component having the weak affinity for the adsorbent while circulatorily flowing the internal fluid without feeding the fluid feed but simultaneously feeding the desorbing fluid into the system.

If desired, following the above-mentioned step (2) can be taken the step (3) of withdrawing the fraction enriched with the component having the weak affinity for the adsorbent from the end of the packed bed unit containing said fraction, and at the same time withdrawing the fraction enriched with the component having the strong affinity for the adsorbent from the end of the packed bed unit containing said fraction and, if further desired, withdrawing the at least one fraction enriched with the component having the intermediate affinity for the adsorbent from the end of the packed bed unit containing said fraction, while at the same time circulating the internal fluid and feeding the fluid desorbent into the system. In this case as well, the position of feeding the above mentioned fluid desorbent and the positions of withdrawing the respective fractions are sequentially shifted downstream of the system in step with the migration of the adsorption zones.

[2] In accordance with still another aspect of the present invention, there is provided a process for separating, or fractioning or isolating, a plurality of components from the mixture thereof in a system comprising a group of a few or more bed units packed with an adsorbent and connected with each other to form an endless, or continuous, series of a circulatory fluid channel in which system a state that a fluid, a liquid in particular, is flowed into the channel or to the outside of the channel while continuously circulating the internal fluid, can be changed into or from a state that the fluid is flowed into the channel or to the outside of the channel while substantially shutting off the internal fluid circulation at at least one position, and in which system a fluid feed having three or more components having respective mutually different affinities for said adsorbent is flowed through said group of packed bed units to separately form an adsorption zone enriched with a component having a weak affinity for the adsorbent, an adsorption zone enriched with a component having a strong affinity for the adsorbent, and at least one adsorption zone enriched with a component having an intermediate affinity for the adsorbent in the order of the strengths of affinity: which process comprises repeating a cycle comprising the step (1) of substantially shutting off the internal fluid circulation at a position of the system immediately upstream of the packed bed unit where the components having the weak and intermediate or strong affinity for the adsorbent coexist, and withdrawing a fraction enriched with the component having an intermediate affinity for the adsorbent from the end of the packed bed unit containing said fraction while feeding the fluid feed from top, or upstream side, of the packed bed unit immediately downstream from the shut-off position, or the second packed bed unit downstream thereof; the step (2) of withdrawing a fraction enriched with the component having the weak affinity for the adsorbent from the end of the packed bed unit containing said fraction and sequentially shifting, in step with the migration of the adsorption zones downstream of the system, the position of feeding the fluid desorbent into the system and the position of withdrawing the fraction enriched with the component having the weak affinity for the adsorbent while circulatorily flowing the internal fluid without feeding the fluid feed but simultaneously feeding the fluid desorbent into the system; and the step (3) of withdrawing the fraction enriched with the component having the weak affinity for the adsorbent from the end of the packed bed unit containing said fraction, and at the same time withdrawing the fraction enriched with the component having the strong affinity for the adsorbent from the end of the packed bed unit containing said fraction while circulating the internal fluid and feeding the fluid desorbent into the system. In this case as well, the position of feeding the above-mentioned fluid desorbent and the positions of withdrawing the respective fractions are sequentially shifted downstream of the system in step with migration of the adsorption zones. If desired, the at least one fraction enriched with the component having the intermediate affinity for the adsorbent is withdrawn, in the step (3), from the end of the packed bed unit containing said fraction while sequentially shifting downstream the position of feeding the fluid desorbent and the positions of withdrawing the respective fractions in step with the migration of the respective adsorption zones.

Additionally stated, the components respectively having the strong, weak and intermediate affinities for the adsorbent may each be a single substance or a mixture of a plurality of substances. For example, in the case where the component having the strong affinity for the adsorbent is B consisting of a mixture of a plurality of substances B1, B2 . . . and their strengths of adsorption for the adsorbent is $B1<B2<\ldots$ , the substances contained in the fluid feed can be regarded as being, for example, a tri-component system wherein the order of the strengths of affinity of component for the adsorbent is A (component having the weak affinity for the adsorbent) $B1<B2$. However, if separation, or isolation, of B1 and B2 from each other is unnecessary, the above-mentioned tri-component system may be considered a di-component system wherein A is a single substance, and B1 and B2 constitute one component.

In the foregoing procedure, the step (1) of the process [1] or [2] is the step of feeding the fluid feed to form a distribution of adsorption zones of respective components to be withdrawn in the following step(s) while at the same time withdrawing out of the system a fraction of component B having a strong affinity from the adsorption zone thereof among the already formed adsorption zones containing the respective fractions enriched with the respective components. The fraction to be withdrawn at this time is not necessarily confined to one fraction. Other fraction(s) enriched with a certain component(s) may also be withdrawn at the same time of withdrawing the fraction enriched with the strong affinity for the adsorbent to enable a large amount of the fractions to be pushed out of the system in a short time.

Additionally stated, the term "shut-off" of the circulation of the system does not necessarily mean complete interception of the circulation channel. It represents a state where the flow of the internal fluid is substantially stagnant at one position of the circulation channel while the fluid feed is fed at a point downstream of such stagnant point and the internal fluid is withdrawn upstream thereof. Provision of a shut-off valve, which can shut off the fluid circulation at the position of the shut-off valve, is generally preferable. In the present invention, such complete "shut-off" of fluid circulation is not necessary. For example, a pump or the like which usually makes it possible to flow a fluid can be controlled so as not to flow a fluid in the direction of circulation to establish the same state as attained by closing a shutoff valve.

The above-mentioned step (2) is the step of feeding the fluid desorbent at a position of the system to withdraw out of the system a fraction enriched with a component other than the component withdrawn in the above-mentioned step (1) (the component having the weak affinity for the adsorbent in the case where the fluid feed is a two-component mixture, and the component of the weaker affinity of the components remaining after the step (1) in the case where the fluid feed is a three- or more-component mixture). Furthermore, the step (2) is to form adsorption zones enriched with respective components contained in a fresh fluid feed fed into the circulatory system and separated in the order of the strengths of affinity for the adsorbent. Specifically, a fluid desorbent is fed upstream of the adsorption zone (from top of the corresponding packed bed unit) wherein the component having the strong affinity for the adsorbent is distributed with circulating the internal fluid by means of a pump(s) and/or the like, while at the same time withdrawing a fraction enriched with the weak affinity for the adsorbent from the downstream side of the adsorption zone thereof (the end of the corresponding packed bed unit). In this case, the position of feeding the fluid desorbent and the position(s) of withdrawing fractions is sequentially shifted downstream in step with the migration of the adsorption zones. The process of the present invention is operable in accordance with the foregoing procedure.

The present invention is principally based on repetition of the cycle comprising the step (1) and the step (2). Needless to say, however, the present invention is operable according to a variety of modified embodiments.

For example, in the case where the fluid feed contains three components, withdrawal of a predetermined component in the above-mentioned step (1) can be carried out not only for one component but also for two or more components. For example, in the case where the fluid feed contains a plurality of components having respective strong affinities for the adsorbent (e.g., B1 and B2), withdrawal of the components having the strong affinities for the adsorbent other than the component A having a weak affinity can be carried out by first withdrawing the component B1 having the relatively weaker affinity for the adsorbent out of the system at a position and subsequently withdrawing the component B2 having a relatively stronger affinity out of the system at the same position. In this case, fractions enriched with the respective components B1 and B2 can be fractionated according to the time-sequential procedure. In the case where fractionation of the components B1 and B2 is unnecessary in particular, they can be withdrawn as a single fraction out of the system.

Additionally stated, in the step (1), not only feeding of the fluid feed but also feeding of the fluid desorbent into the system is possible to provide an advantage that the feeding amount of the fluid feed can be controlled together with the withdrawing amount of the component having a strong affinity for the adsorbent (control of mass balance). Particularly, feeding of the fluid desorbent into the system increases the flow rate of the internal fluid downstream of the desorbent-feeding position to provide another advantage that a choice can be made of the migration rate(s) of the adsorption zone(s) of the predetermined component(s). For example, when the fluid desorbent is fed, at a position upstream of the adsorption zone of the component B2 having the strongest affinity for the adsorbent, to the adsorption system wherein the adsorption zones of a tri-component mixture of the fluid feed has already been respectively formed of the components each having a weak to strong affinity for the adsorbent (tentatively, three components A, B1 and B2) and sequentially separated in the order thereof, the migration of the components A', B1' and B2' of a freshly fed fluid feed as well as the migration of the component A having the weakest affinity for the adsorbent and located just downstream of the shut-off position can be carried out at respective rates corresponding to the amount of the fluid feed being fed into the system, while at the same time the migration of the adsorption zone of the component B2 having the strongest affinity for the adsorbent as well as withdrawal of the fraction enriched with the component B1 can be carried out at rates synergistically increased by the feeding rate of the above-mentioned fluid feed and the feeding rate of the fluid desorbent. This enables the adsorption zone of the component A having the weak affinity for the adsorbent (having a high migration rate) and distributed downstream of the shut-off position to be effectively prevented from catching up with the adsorption zone of the component B2 having the strong affinity for the adsorbent (having a slow migration rate). Additionally stated, feeding of the fluid desorbent into the system may be either simultaneous or sequential with feeding of the fluid feed into the system. If the above-mentioned component B1 is considered a component B having the intermediate affinity for the adsorbent while the component B2 is considered a component C having the strong affinity for the adsorbent, the system is considered a tri-component system essentially consisting of the components A, B and C.

Furthermore, in the step (1), there can be carried out not only withdrawal of the fraction enriched with the component having the strong affinity for the adsorbent, but also simultaneous withdrawal of a fraction enriched with another component at a predetermined position.

Repetition of an operation of the aforementioned steps (1) and (2) represents a state wherein equipment therefor is continuously operated. However, before starting up the equipment it is necessary to carry out, prior to the step (1), a preliminary step of feeding to the system a fluid feed containing three or more components having respective different affinities for the adsorbent to form adsorption zones sequentially separated into respective fractions enriched with the respective components having weak to strong affinities for the adsorbent in the order thereof. Needless to say, this preliminary step may be taken by repeating the procedure similar to the aforementioned steps (1) and (2) and, if desired, (3) according to the present invention. However, the contents of the respective fractions withdrawn out of the system in the preliminary step is, needless to say, different from those contents of the fractions withdrawn out of the system in the steady state of the steps.

In the present invention, the step (3) may further be taken following the above-mentioned step (2). More specifically, the step (3) is such that, while circulating the internal fluid in the above-mentioned system, the fluid desorbent is fed into the system, and at the same time at least two fractions enriched with the respective components are withdrawn out of the system; and such that the positions of feeding the fluid desorbent into the system and the positions of withdrawing those fractions are sequentially shifted downstream in the direction of the circulation of the fluid in step with the migration of the adsorption zones of the fractions enriched with the respective components.

This step (3) is taken from the time when the components contained in the fluid feed fed into the system in the step (1) are migrated downstream by the step (2) to form the adsorption zones enriched with the respective components to such an extent that separation of the components has proceeded to form the adsorption zones of fractions enriched with the components having the respective weak to strong affinities for the adsorbent and separated in the order thereof, whereby the fraction enriched with the component having the strong affinity for the adsorbent can be withdrawn out of the system. The significance of taking the step (3) lies in that the adsorption zones wherein desired separation of components has already been attained to an aimed extent are circulatorily migrated to the completed positions of a predetermined cycle, while at the same time continuously withdrawing two or more desired fractions out of the system. Industrial chromatographic separation equipment is usually designed for a particular application or a certain object system to be subjected to separation. However, there is a strong demand for using a single assembly of chromatographic separation equipment for a plurality of object systems. For example, in the case where a fluid feed containing four components (e.g., A, B1, B2 and B3) is fractionated into four fractions each substantially containing a single component by using the process of the present invention and equipment therefor, in the first stage three components A, B1 and B2 are fractionated into one fraction, while the remaining component B3 is also fractionated into one fraction. In the second stage, the mixed fluid of the single fraction containing the three components A, B1 and B2 withdrawn out of the system in the first stage is fed into the same equipment to be separated into three fractions A, B1 and B2 enriched with the respective components The foregoing procedure can be mentioned as using the same equipment for a plurality of object systems. In such a case, the easiness, or difficulty, in separation of the components in the first stage is different from that in the separation in the second stage.

Where equipment designed to be adapted for highly difficult separation of components is used for an object system easy of separation of components, there may be a possibility that desired separation of adsorption zones enriched with the respective components is completed in the course of the step (2) before the adsorption zones reach the predetermined positions at which one cycle is completed. In this case, although the step (2) may be further continued, fluid circulation should necessarily be carried out without withdrawing a fraction from an adsorption zone enriched with a component having a strong affinity for the adsorbent, thereby broadening the above-mentioned adsorption zone. This results in being incapable of preventing the component having the strong affinity for the adsorbent from avoiding dilution thereof.

The step (3) adds to the process an advantage that the flow rate upstream of the position of withdrawing a fraction from the corresponding adsorption zone enriched with the component having the strong affinity for the adsorbent is increased by adding the step (3) of withdrawing the fraction from the corresponding adsorption zone enriched with the component having the strong affinity for the adsorbent following the step (2) of the process, while at the same time the flow rate downstream of the position of withdrawing the fraction from the corresponding adsorption zone enriched with the component having the strong affinity for the adsorbent is decreased. This results in being capable of preventing the adsorption zone enriched with the component having the strong affinity for the adsorbent from broadening to enter the forward as well as backward zone. In short, a piece of equipment which is so designed that it can take the step (3) increases the possibility of applying a single assembly of equipment for a plurality of object systems to be subjected to separation of components thereof.

In the step (2) and/or (3) of the process of the present invention, the flow rate of a fluid to be circulated in the system can be gradually or step-wise increased. This represents an improvement in productivity and provides a preferable method in the case where the object system to be subjected to separation of components thereof is a fluid having a property of increasing the viscosity thereof in keeping with an increase in the concentration thereof, examples of which include solutions of saccharides. This results from the fact that the fluid feed is fed into the system only in the step (1), while the fluid desorbent is fed into the system only in the steps (2) and (3) to only withdraw the separated component(s) out of the system, with the result that the concentration(s) of the component(s) as the target(s) of separation is usually decreased with the lapse of time. In other words, the decrease in the concentration lowers the viscosity of fluid and therefore the pressure loss in an adsorbent layer if the flow rate of circulation is constant. Operating the system at higher flow rates which lead to the upper limit of pressure loss allowable for the equipment results in shortening the time of one cycle to thereby improve the productivity. In this case, the flow rate of a fraction withdrawn out of the system as well as the flow rate of the fluid desorbent fed into the system should better be increased. Usually, these flow rates are increased substantially in proportion with an increase in the flow rate of the internal fluid.

The process of the present invention can be applied to fractionation, or separation, of two or more components contained in a gas or a liquid. Particularly a large amount of a fluid can be treated to be separated into fractions of components thereof on an industrial scale according to the present invention. Equipment for the process of the present invention is quite useful as industrial equipment for refining of sacchrides and homologues thereof in particular such as a variety of saccharides and sugaralcohols by making use of an adsorbent such as a strongly acidic cation exchange resin of alkaline metal type or alkaline earth metal type. Examples of object systems to be subjected to such refining include molasses to be separated into useful substances such as sucrose, raffinose, betaine and inositol; isomerized saccharide to be separated into glucose and fructose; a liquid mixture containing lactose, lactulose and galactose to be separated into the respective components; a liquid mixture containing glucose, sucrose, fructooligosaccharides to be separated into the respective components; a liquid mixture containing glucose, isomaltose and isomaltodextrine to be separated into the respective components; a liquid mixture containing glucose, maltose and maltodextrine to be separated into the respective components; and a liquid mixture containing sugaralcohols such as sorbitol and maltitol to be separated into the respective components.

According to the present invention, a liquid mixture or the like containing two components or three or more components can be efficiently separated into at least two fractions enriched with the respective components.

Particularly, simple equipment can be effectively used for separation of three or more components from the mixture thereof, which separation is said to be impossible using prior art simulated moving bed equipment.

According to the present invention, the amount of the adsorbent to be used may be small to lead to smaller unit amount of the adsorbent, of an object system to be separated into fractions. This very effectively leads to a favorable, large scale, industrial operation of equipment.

BRIEF DESCRIPTION OF THE DRAWINGS

The foregoing and other objects, features and advantages of the present invention will be better understood from the following description taken in connection with the accompanying drawings in which.

BEST MODES FOR CARRING OUT THE INVENTION

The present invention will be more specifically described by Examples, which, of course, does not limit the scope of the invention in so far as any departure from the subject matter of the present invention does not ensue.

Figure 1:
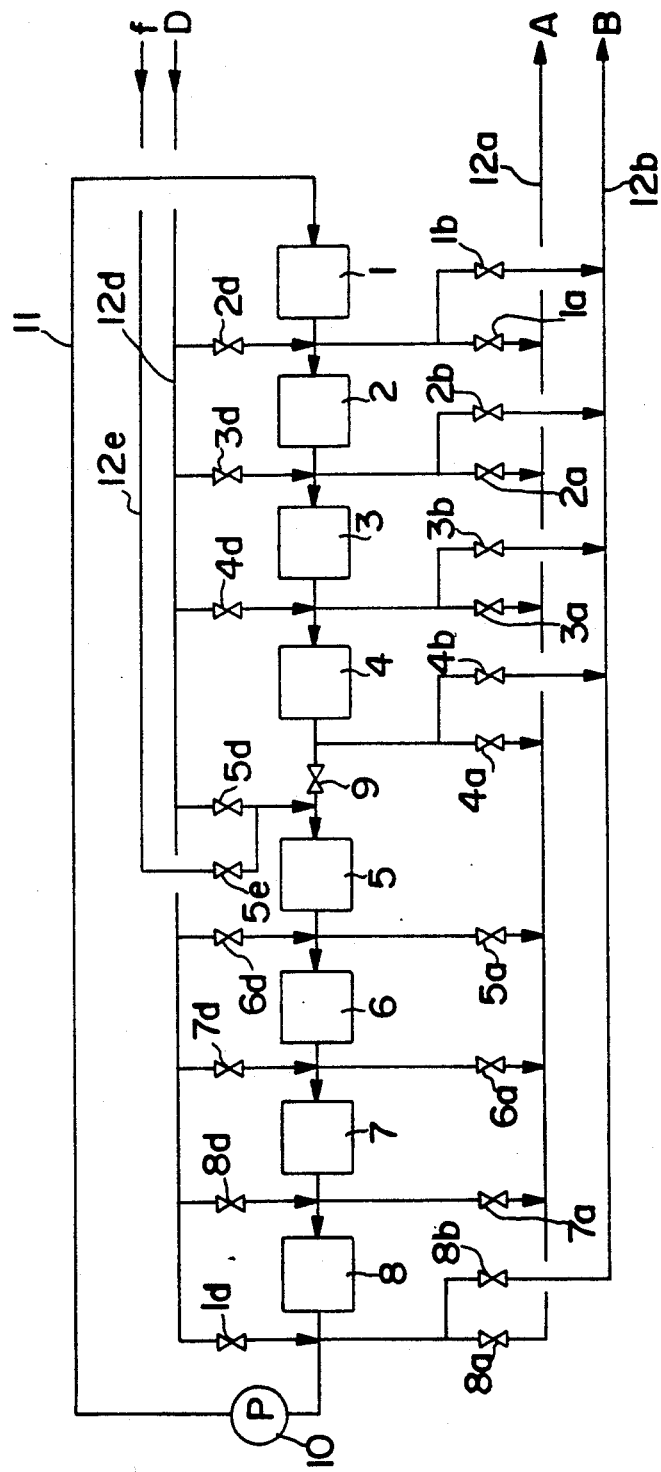
FIG. 1 is a schematic illustration of an example of equipment by means of which the process of the present invention is operable.

FIG. 1 is an example of the profile of equipment by means of which the process of the present invention is operable. In this figure, bed units 1 to 8 are packed with the same adsorbent. The packed bed units 1 to 8 are linked with each other by pipings to enable a fluid, a liquid in particular, to be flowed therebetween, while the latter, or downstream end of the last stage packed bed unit 8 is connected with the upstream end of the first packed bed unit 1 via liquid channel 11. Additionally stated, a pump 10 is provided halfway of the liquid channel 11 to effect circulation of the liquid. The flow rate can be set at predetermined value by means of a flow rate controller which is not shown in the figure. Such a pump may be provided singly anywhere between any packed bed units. Alternatively, a plurality of pumps may be provided anywhere between any packed bed units, as desired.

A shut-off valve 9 is provided halfway of a linking piping between the packed bed units 4 and 5, and can be controlled to be opened or closed by means of a shut-off valve controller which is not shown in the figure.

A fluid, or liquid in particular, feeding pipe is connected to the linking piping downstream of the shut-off valve 9 between the packed bed units 4 and 5, and linked with a liquid feed feeding piping 12e via the liquid feed feeding valve 5e, while being linked with a piping 12d for feeding an eluant (common for all components) as the fluid desorbent via an eluant feeding valve 5d. Liquid withdrawal pipes for withdrawing fractions out of the system are connected with the pipings between the packed bed units upstream of the above-mentioned shut-off valve 9, and each branched into two pipings to enable two fractions enriched with respective components to be fractionated as will be described hereinafter. For example, in the case of two fractions respectively enriched with a component having a weak affinity for an adsorbent (hereinafter referred to as a component A) and a component having a strong affinity for the adsorbent (hereinafter referred to as a component B), a pipe just upstream of the shut-off valve 9 is connected with common withdrawal pipes 12a and 12b (each common for the same component) via withdrawal valves 4a and 4b.

A common eluant feeding piping 12d is linked with the packed bed units 1 to 8 via eluant feeding valves 2d, 3d, 4d, 6d, 7d, 8d and 1d disposed between the packed bed units 1 and 2, 2 and 3, 3 and 4, 5 and 6, 6 and 7, 7 and 8, and 8 and 1, respectively. These eluant feeding valves can be adequately switched to be opened or closed together with the aforementioned eluant feeding valve 5d and the liquid feed feeding valve 5e by means of a valve controller which is not shown in the figure.

Also, liquid withdrawal pipes are connected to the packed bed units 1 to 8 between the packed bed units 1 and 2, 2 and 3, 3 and 4, 5 and 6, 6 and 7, 7 and 8, and 8 and 1 as in the case of feeding valves. In the case of the packed bed units 1 to 4, the liquid withdrawal pipes therebetween are respectively connected with common withdrawal pipings 12a and 12b via withdrawal valves 1a to 3a and withdrawal valves 1b to 3b for respectively withdrawing the components A and B. In the case of the packed bed units 5 to 8, the liquid withdrawal pipes therebetween are respectively connected with common withdrawal piping 12a via withdrawal valves 5a to 7a for withdrawing the component A. The liquid withdrawal pipe between the packed bed units 8 and 1 is connected with the common withdrawal pipings 12a and 12b via withdrawal valves 8a and 8b for respectively withdrawing the components A and B. These withdrawal pipes can be adequately switched to be opened or closed together with the aforementioned withdrawal valves 4a and 4b by means of withdrawal valve controller which is not shown in the figure. FIG. 1 is only an example of the profile of the structure of equipment by means of which the process of the present invention is operable. Depending on the object system to be subjected to separation of the components thereof, needless to say, another withdrawal valve(s) for withdrawing the component B, another fluid feed feeding valve(s) and another shut-off valve(s) may be added, or the number of withdrawal valves for withdrawing the component B may be decreased.

Although the equipment as shown in FIG. 1 is provided with the eight packed bed units, the number of such packed bed units may be varied depending on the kind of object mixture to be subjected to separation of the components thereof and the purpose of fractional separation. In general, the number of packed bed units is 3 to 36, preferably 3 to 24, more preferably 3 to 16.

Figure 2:
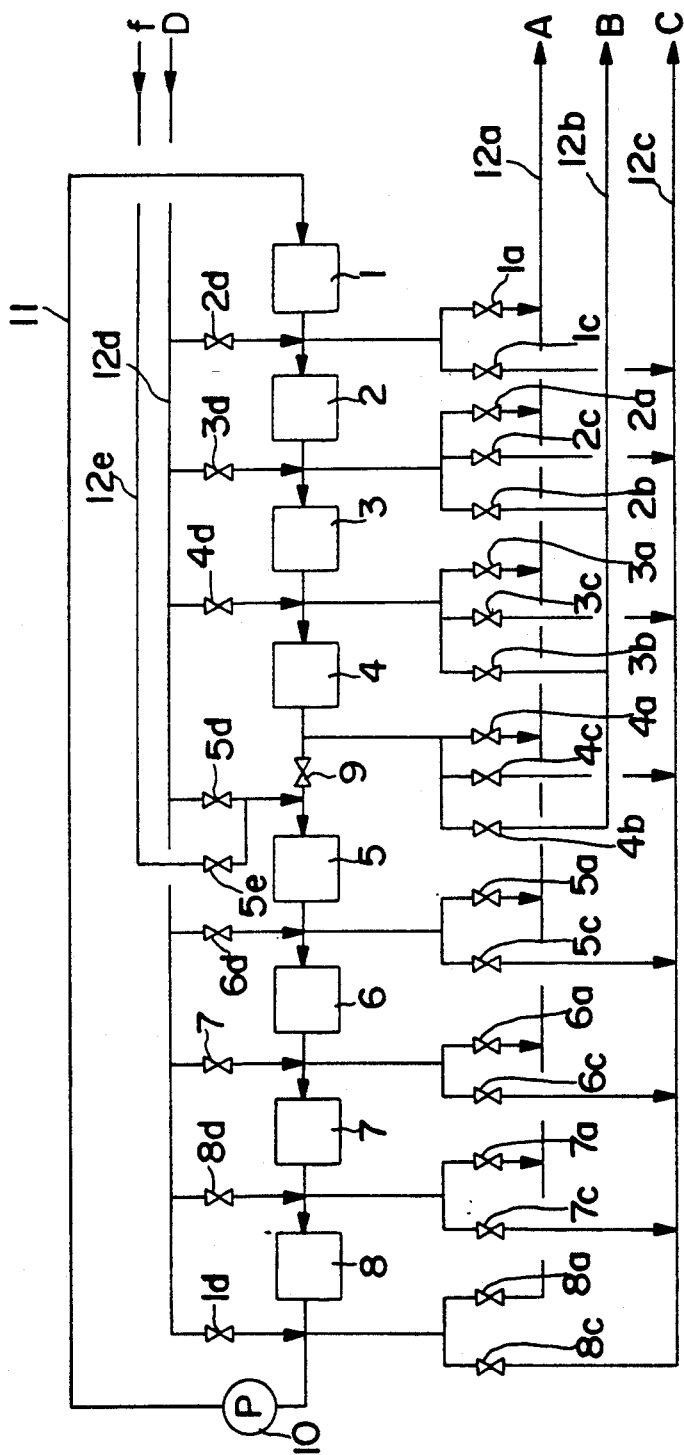
FIG. 2 is a schematic illustration of another example of equipment by means of which the process of the present invention is operable.

FIG. 2 shows equipment for separation of three components which includes pipings B and C for withdrawing components respectively having intermediate and strong affinities for an adsorbent.

Three components contained in the liquid mixture thereof is separated into three fractions enriched with the respective components by using the equipment as shown in FIG. 2 in accordance with a flow chart as shown in FIG. 3. Additionally stated, FIG. 3 is a case where the component B consists of two components B1 and B2 (A, B1 and B2 in total). In this case, however, separation of two components can be carried out in accordance with the flow chart in the case where the component B is single or in the case the component B is two or more components but separation thereof is not industrially necessary so that these components can be handled as one component. In the latter case, the components B1 and B2 may be considered a is carried out in practice.

Figure 3A:
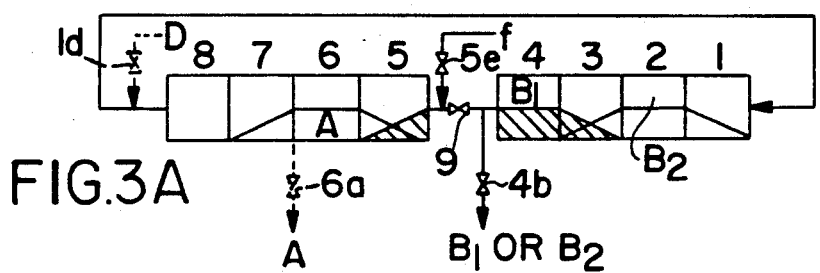
FIGS. 3A-3I are a flow chart illustrating the working of the equipment of FIG. 1 in association with feeding and withdrawal of liquids in conjunction with timely opening and closing of valves.

FIG. 3A is a model diagram showing a state that a fluid feed f is introduced into a packed bed unit 5 via a fluid feed feeding valve 5e positioned downstream of a shutoff valve 9 in a closed state, while at the same time an eluant (fluid desorbent) D is fed into the system via a eluant feeding valve 1d positioned upstream of the component B2, whereby the component B1 has started to be withdrawn out of the system via the withdrawal valve 4b positioned upstream of the shut-off valve 9. At the same time, the component A may be withdrawn out of the system via the withdrawal valve 6a as shown by the broken line in FIG. 3A.

Figure 3B:
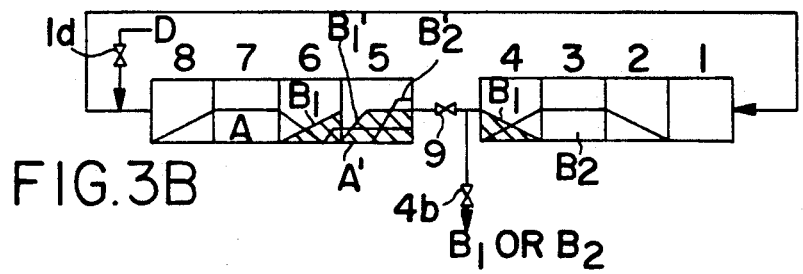

FIG. 3B is a model diagram showing a state that the eluant D is fed into the system via the eluant feeding valve 1d to further withdraw the components B1 and B2 upstream of the closed shut-off valve 9. In this figure, A', B1' and B2' denotes the components A, B1 and B2 contained in the fluid feed fed into the system in the step as shown in FIG. 3A.

FIG. 3 (1-1) corresponds to the step (1) of the process of the present invention wherein a fluid feed, a liquid feed in particular, is flowed into the system while at the same time a fluid desorbent, an eluant in particular, is flowed into the system. FIG. 3B corresponds to the stage of prolonging feeding of the eluant to withdraw a larger amount of the components B1 and B2 out of the system. Therefore, this stage can sometimes be omitted depending on the object system to be subjected to separation of the components thereof.

Figure 3C:
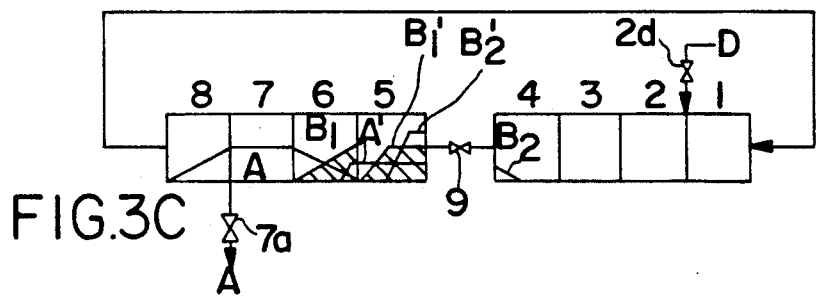
Figure 3D:
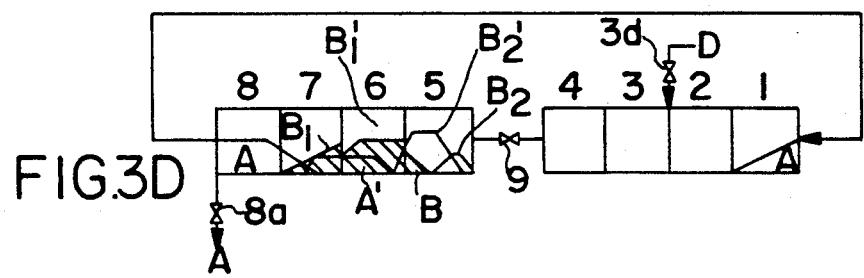
Figure 3E:
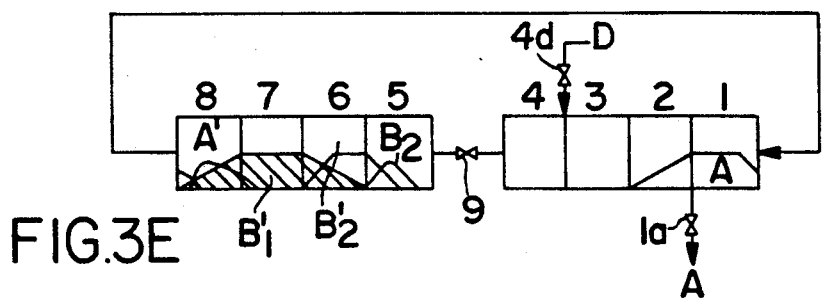
Figure 3F:
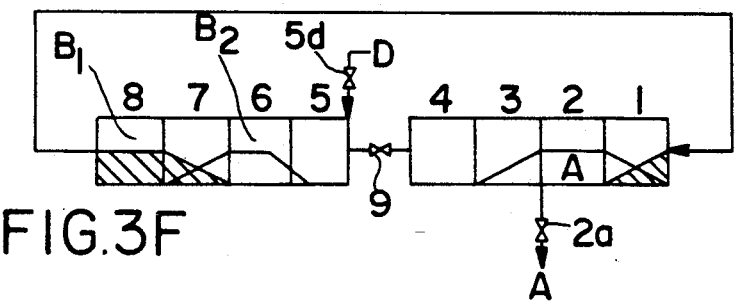
Figure 3G:
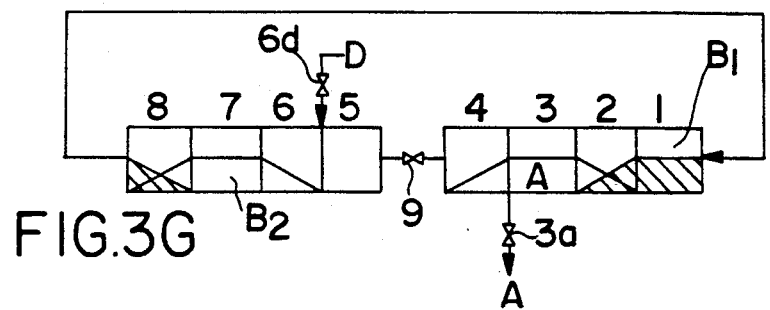
Figure 3H:
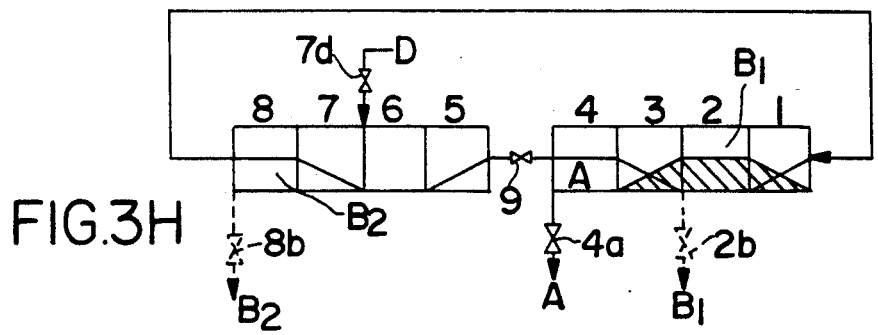
Figure 3I:
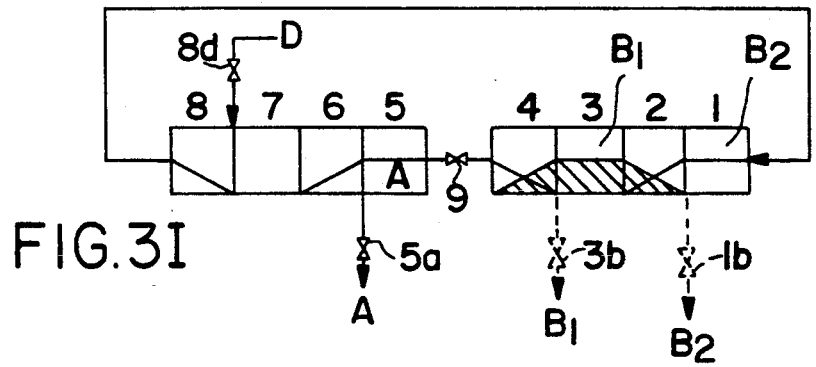
Figure 4:
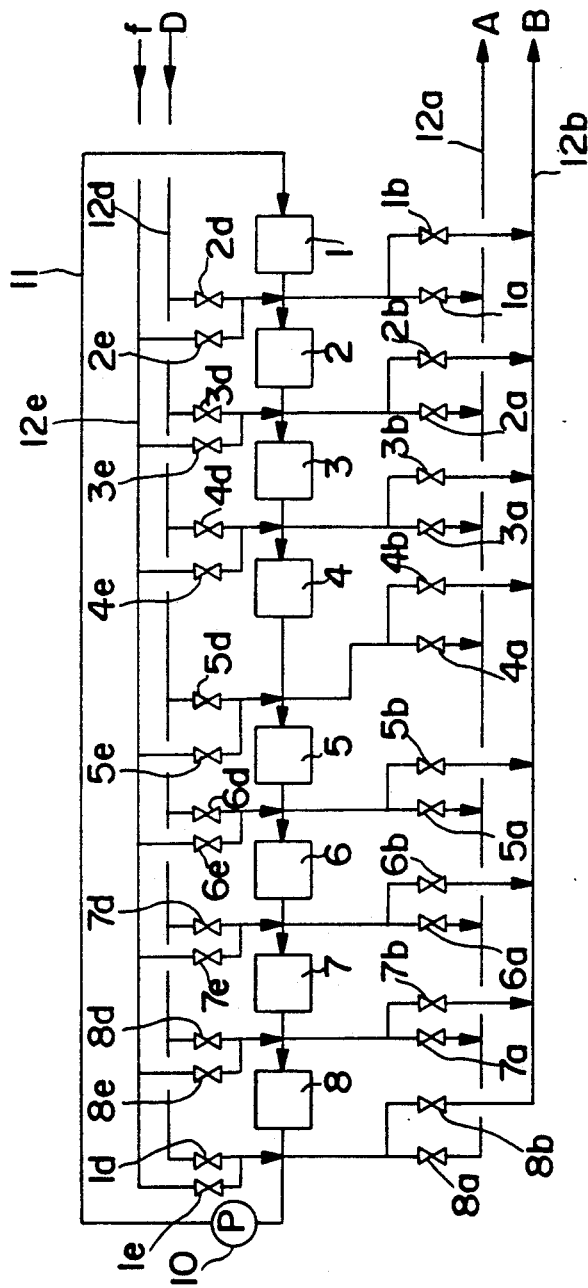
FIG. 4 is a schematic illustration of an example of the conventional simulated moving bed equipment for factionation of two components.

FIGS. 3C ti U corresponds to the step (2) of the process of the present invention. With the shut-off valve 9 opened and without feeding the fluid feed f into the system, feeding of the eluant D and withdrawal of component A are carried out while circulating the internal fluid throughout the system in accordance with the simulated moving bed procedure. FIGS. 3 (2-1) to (2-7) are model diagrams showing sequential operations of shifting downstream the position of feeding the eluant into the system and the position of withdrawing the component A out the system.

In Figs. 3A and I, the components B2 and/or B1 may be withdrawn out of the system as shown by the broken lines. This corresponds to the step (3) of the process of the present invention.

Furthermore, in carrying out the step (3), the component B may be withdrawn as the component B1 without withdrawal of the component B2 in the step (1), and may be withdrawn as the component B2 only in the step (3) to effect separation of the three fractions.

The present invention provides a process for separating two or more fractions from a mixture containing two or more components. In general, however, the number of fractions separated from each other is preferably 2 to 16, more preferably 2 to 6, most preferably 2 to 3.

EXAMPLE 1

This Example is related to separation of glucose and fructose contained in a mixture. The equipment as shown in FIG. 1, a strongly acidic cation exchange resin in the Ca form (Amberlite CG6000: trade name of a product manufactured by Rohm and Haas Co.) as an adsorbent, and water as an eluant were used to carry out chromatographic separation of a liquid feed (solution of isomerized saccharide as shown in Table 1).

TABLE 1

| Concentration | Composition [Solids Content, %] | | |
|---|---|---|---|
| [%] | oligosaccharides | glucose | fructose |
| 60.0 | 5% | 53% | 42% |

A simulated moving bed packed with 73.7 l in total of the adsorbent and consisting of 8 packed bed units linked with each other in an endless, or continuous, series and having an inner diameter of 108.3 mm and a packed bed height of 1,000 mm was kept at an inside temperature of 60° C. to repeat therein chromatographic separation in accordance with a time schedule as shown in Table 2. In this Example, the affinities of the components for the adsorbent were in the order of fructose > glucose > oligosaccharides. A liquid fraction enriched with glucose was withdrawn out of the system via the fraction withdrawal valves 1a to 8a, and a liquid fraction enriched with fructose was withdrawn out of the system via the fraction withdrawal valve 4b.

Various flow rates in the steps (1) and (2) were as follows.

| Flow Rates in the Step (1) | |
|---|---|
| feeding flow rate of liquid feed | 27.64 l/hr |
| feeding flow rate of eluant | 9.21 l/hr |
| withdrawal flow rate of glucose fraction | 5.07 l/hr |
| withdrawal flow rate of fructose fraction | 31.78 l/hr |
| Flow Rates in the Step (2) [Stages (2) and (3)] | |
| feeding flow rate of eluant (withdrawal flow rate of fructose fraction) | 5.07 l/hr |
| circulation flow rate between position of feeding eluant and position of withdrawing glucose fraction | 27.64 l/hr |
| Flow rate in the Step (2) [Stages (4) to (8)] | |
| feeding flow rate of eluant (withdrawal flow rate of fructose fraction) | 10.16 l/hr |
| circulation flow rate between position of feeding eluant and position of withdrawing glucose fraction | 55.3 l/hr |

TABLE 2

| Step | Stage | Fed Liquid | Withdrawn Liquid | No. of Open Valve | Time (min) |
|---|---|---|---|---|---|
| 1 | 1 | feed, water | glucose fraction fructose fraction | 5e, 1d, 6a 4b | 14.4 |
| 2 | 2 | water | glucose fraction | 9, 2d, 7a | 14.4 |
|   | 3 | water | glucose fraction | 9, 3d, 8a | 14.4 |
|   | 4 | water | glucose fraction | 9, 4d, 1a | 7.2 |
|   | 5 | water | glucose fraction | 9, 5d, 2a | 7.2 |
|   | 6 | water | glucose fraction | 9, 6d, 3a | 7.2 |
|   | 7 | water | glucose fraction | 9, 7d, 4a | 7.2 |
|   | 8 | water | glucose fraction | 9, 8d, 5a | 7.2 |

After 14 cycles of a procedure as shown in the time schedule of Table 2 wherein the above-mentioned flow rates were used, the compositions of the fractions obtained in the 14th cycle of the procedure are listed in Table 3.

TABLE 3

|  | Concentration | Composition [Solids Content, %] | | |
|---|---|---|---|---|
|  | [%] | oligosaccharides | glucose | fructose |
| Glucose | 26.5 | 6.8% | 89.9% | 3.4% |

TABLE 3-continued

| | Concentration [%] | Composition [Solids Content, %] | | |
|---|---|---|---|---|
| | | oligosaccharides | glucose | fructose |
| Fraction Fructose Fraction | 26.6 | 2.7% | 6.3% | 91.0% |

EXAMPLE 2

This example is related to separation of oligosaccharides and glucose contained in a mixture.

The same equipment as used in Example 1, a strongly acidic cation exchange resin in the Na form (Amberlite CG6000: trade name of a product manufactured by Rohm and Haas Co.) as an adsorbent, and water as an eluant where used to carry out chromatographic separation of a liquid feed (solution of a mixture of oligosaccharides, maltose and glucose) as shown in Table 4.

TABLE 4

| Concentration [%] | Composition [Solids Content, %] | | |
|---|---|---|---|
| | oligosaccharides | maltose | glucose |
| 60 | 18% | 77% | 5% |

The simulated moving bed packed with 73.7 l in total of the adsorbent and comprising 8 packed columns linked with each other in an endless, or continuous, series and having a packed bed unit height of 1,000 mm was kept at an inside temperature of 70° C. to repeat therein the chromatographic separation in accordance with a time schedule as shown in Table 5. In this Example, the affinities of the components for the adsorbent were in the order of glucose <maltose <oligosaccharides. A liquid fraction enriched with oligosaccharides was withdrawn out of the system via the the fraction withdrawal valves 1a to 8a. A liquid fraction enriched with glucose was withdrawn out of the system via the fraction withdrawal valve 1b to 2b. A liquid fraction enriched with maltose was first withdrawn out of the system via the fraction withdrawal valve 4b, and a liquid fraction enriched with glucose was subsequently withdrawn out of the system via the same withdrawal valve 4b.

Various flow rates in the steps (1), (2) and (3) are as follows.

| Flow Rates in the Step (1) | |
|---|---|
| feeding flow rate of liquid feed | 27.6 l/hr |
| feeding flow rate of eluant | 64.49 l/hr |
| withdrawal flow rate of oligosaccharide fraction | 14.76 l/hr |
| withdrawal flow rate of maltose fraction and gulcose fraction | 77.33 l/hr |
| Flow Rates in the Step (2) [Stages (3) and (4)] | |
| feeding flow rate of eluant (withdrawal flow rate of oligosaccharide fraction) | 7.36 l/hr |
| circulation flow rate between position of feeding eluant and position of withdrawing oligosaccharide fraction | 27.6 l/hr |
| Flow rate in the Step (2) [Stages (5) to (7)] | |
| feeding flow rate of eluant (withdrawal flow rate of oligosaccharide fraction) | 14.72 l/hr |
| circulation flow rate between position of feeding eluant and position of withdrawing oligosaccharide fraction | 55.3 l/hr |
| Flow rate in the Step (3) | |
| feeding flow rate of eluant | 19.78 l/hr |
| withdrawal flow rate of oligosaccharide fraction | 14.72 l/hr |
| withdrawal flow rate of glucose fraction | 5.06 l/hr |

-continued

| | |
|---|---|
| circulation flow rate between position of feeding eluant and position of withdrawing glucose fraction | 60.4 l/hr |

TABLE 5

| Step | Stage | Fed Liquid | Withdrawn Liquid | No. of Open Valve | Time (min) |
|---|---|---|---|---|---|
| 1 | 1 | feed, water | oligosaccharide fraction maltose fraction | 5e, 2d, 7a 4b | 3.83 |
| 2 | 2 | feed, water | oligosaccharide fraction glucose fraction | 5e, 2d, 7a 4b | 4.18 |
| | 3 | water | oligosaccharide fraction | 9, 3d, 8a | 10.7 |
| | 4 | water | oligosaccharide fraction | 9, 4d, 1a | 10.7 |
| | 5 | water | oligosaccharide fraction | 9, 5d, 2a | 5.34 |
| | 6 | water | oligosaccharide fraction | 9, 6d, 3a | 5.34 |
| | 7 | water | oligosaccharide fraction | 9, 7d, 4a | 5.34 |
| 3 | 8 | water | oligosaccharide fraction glucose fraction | 9, 8d, 5a 1b | 5.34 |
| | 9 | water | oligosaccharide fraction glucose fraction | 9, 1d, 6a 2b | 5.34 |

After 18 cycles of a procedure as shown in the time schedule of Table 5 wherein the above-mentioned flow rates were used, the compositions of the fractions obtained in the 18th cycle of the procedure are listed in Table 6.

TABLE 6

| | Concentration [%] | Composition [Solids Content, %] | | |
|---|---|---|---|---|
| | | oligo-saccharides | maltose | glucose |
| Oligosaccharide Fraction | 5.0 | 80.4% | 19.3% | 0.3% |
| Maltose Fraction | 37.0 | 2.1% | 94.3% | 3.6% |
| Glucose Fraction | 1.5 | 10.8% | 23.1% | 66.1% |

In the foregoing two Examples, the respective liquid feeds containing three or more components as object systems to be subjected to chromatographic separation were each separated into two or three fractions, demonstrating good results of separation that can not be attained by any conventional processes and equipment.

What is claimed is:

1. A process for fractional separation of a plurality of components from the mixture thereof in a system comprising a group of a number of packed bed units packed with an adsorbent and connected with each other to form an endless, or continuous, series of a circulatory fluid channel in which system a state that a fluid is flowed into said channel or to the outside of said channel while continuously circulating the internal fluid, can be changed either into or from a state that said fluid is flowed into said channel or to the outside of said channel while substantially shutting off the internal fluid circulation at at least one position of the channel, or system, and in which system a fluid feed containing two components having respective mutually different affinities for said adsorbent is flowed through said group of packed bed units to separately form an adsorption zone enriched with a component having a weak affinity for said adsorbent and an adsorption zone enriched with a component having a strong affinity for said adsorbent: which process comprises repeating a cycle comprising a step (1) of substantially shutting off the internal fluid circulation at at least one position of said system immediately upstream of the packed bed unit where the components having the weak and intermediate or strong affinity for the adsorbent coexist, and withdrawing a fraction enriched with said component having the strong affinity for said adsorbent while feeding the fluid feed from top, or upstream side, of the packed bed unit immediately downstream of the shut-off position or the second packed bed unit downstream thereof; and a step (2) of withdrawing said fraction enriched with said component having the weak affinity for said adsorbent and remaining in the system after the step (1) above and sequentially shifting, in step with the migration of the adsorption zones downstream of the system, the position of feeding a fluid desorbent into the system and the position of withdrawing the fraction enriched with the component having the weak affinity for said adsorbent while circulatorily flowing the internal fluid without feeding the fluid feed but simultaneously feeding the fluid desorbent into the system.

2. A process for fractional separation of a plurality of components from the mixture thereof as claimed in claim which process further comprises, following said step (2), a step (3) of continuing withdrawing the fraction enriched with said component having the weak affinity for said adsorbent from the end of the packed bed unit containing said fraction and at the same time withdrawing the fraction enriched with said component having the strong affinity for said adsorbent from the end of the packed bed unit containing said fraction mentioned just above while circulating the internal fluid, feeding the fluid desorbent into the system, and shifting downstream the position of feeding the fluid desorbent and the positions of withdrawing the respective fractions in step with the migration of the respective adsorption zones.

3. A process for fractional separation of a plurality of components from the mixture thereof in a system comprising a group of a number of packed bed units packed with an adsorbent and connected with each other to form an endless, or continuous, series of a circulatory fluid channel in which system a state that a fluid is flowed into said channel or to the outside of said channel while continuously circulating the internal fluid, can be changed either into or from a state that the fluid is flowed into said channel or to the outside of said channel while substantially shutting off the internal fluid circulation at at least one position of the channel, or system, and in which system a fluid feed having three or more components having respective mutually different affinities for said adsorbent is flowed through said group of packed bed units to separately form an adsorption zone enriched with a component having a weak affinity for said adsorbent, an adsorption zone enriched with a component having a strong affinity for said adsorbent and at least one adsorption zone enriched with a component having an intermediate affinity for said adsorbent: which process comprises repeating a cycle comprising a step (1) of substantially shutting off the internal fluid circulation at at least a position of said system immediately upstream of the packed bed unit where the components having the weak and intermediate or strong affinity for the adsorbent coexist, and sequentially withdrawing, from the same position in the system, a fraction enriched with said component having the intermediate affinity for said adsorbent and a fraction enriched with said component having the strong affinity for said adsorbent while feeding the fluid feed from top, or upstream side, of the packed bed unit, immediately downstream of the shut-off position or the second packed bed unit downstream thereof; and a step (2) of withdrawing the fraction enriched with said component having the weak affinity for said adsorbent and remaining in the system after the step (1) above and sequentially shifting, in step with the migration of the adsorption zones downstream of the system, the position of feeding a fluid desorbent into the system and the position of withdrawing the fraction enriched with said component having the weak affinity for said adsorbent while circulatorily flowing the internal fluid without feeding the fluid feed but simultaneously feeding the fluid desorbent into the system.

4. A process for fractional separation of a plurality of components from the mixture thereof as claimed in claim 3: which process further comprises, following said step (2), the step (3) of withdrawing the fraction enriched with said component having the weak affinity for said adsorbent from the end of the packed bed unit containing said fraction, and at the same time withdrawing a fraction enriched with said component having the strong affinity for said adsorbent from the end of the packed bed unit containing said fraction mentioned just above, and, if desired, withdrawing a fraction enriched with the component having intermediate affinity for said adsorbent from the end of the packed bed unit containing said fraction mentioned just above, while at the same time circulating the internal fluid and feeding the fluid desorbent into the system and sequentially shifting, in step with the migration of the adsorption zones downstream of the system, the position of feeding said fluid desorbent and the positions of withdrawing the respective fractions.

5. A process for fractional separation of a plurality of components from the mixture thereof in a system comprising a group of a number of packed bed units packed with an adsorbent and connected with each other to form an endless, or continuous, series of a circulatory fluid channel in which system a state that a fluid is flowed into said channel or to the outside of said channel while continuously circulating the internal fluid, can be changed either into or from a state that said fluid is flowed into said channel or to the outside of said channel while substantially shutting off the internal fluid circulation at at least one position of the channel, or system, and in which system a fluid feed having three or more components having respective mutually different affinities for said adsorbent is flowed through said group of packed bed units to separately form an adsorption zone enriched with a component having a weak affinity for said adsorbent, an adsorption zone enriched with a component having a strong affinity for said adsorbent and at least one adsorption zone enriched with a component having an intermediate affinity for said adsorbent: which process comprises repeating a cycle comprising a step (1) of substantially shutting off the internal fluid circulation at at least a position of said system immediately upstream of the packed bed unit where the components having the weak and intermediate or strong affinity for the adsorbent coexist, and withdrawing a fraction enriched with said component having the intermediate affinity for said adsorbent from the end of the packed bed unit containing said fraction mentioned just above, while feeding the fluid feed from top, or upstream side, of the packed bed unit immediately downstream of the shut-off position or the second packed bed unit downstream thereof;

a step (2) of withdrawing said fraction enriched with said component having the weak affinity for said adsorbent from the end of the packed bed unit containing said fraction mentioned just above and sequentially shifting, in step with the migration of the adsorption zones downstream of said system, the position of feeding the fluid desorbent into the system and the position of withdrawing the fraction enriched with the component having the weak affinity for said adsorbent, while circulatorily flowing the internal fluid without feeding the fluid feed but simultaneously feeding a fluid desorbent into the system; and a step (3) of withdrawing the fraction enriched with the component having the weak affinity for said adsorbent from the end of the packed bed unit containing said fraction enriched with said component having the weak affinity for said adsorbent, and at the same time withdrawing the fraction enriched with said component having the strong affinity for said adsorbent from the end of the packed bed unit containing said fraction mentioned just above, and, if desired, withdrawing said at least one fraction enriched with the component having the intermediate affinity for the adsorbent from the end of the packed bed unit containing said fraction enriched with said component having the intermediate affinity for said adsorbent, while at the same time circulating the internal fluid and feeding the fluid desorbent into the system and sequentially shifting, in step with the migration of the adsorption zones, the position of feeding said fluid desorbent and the positions of withdrawing the respective fractions.

6. A process for fractional separation of a plurality of components from the mixture thereof as claimed in any one of claims 1 to 5, wherein the fraction enriched with said component having the weak affinity for said adsorbent is simultaneously withdrawn, in the step (1), from the end of the packed bed unit wherein the adsorption zone enriched with said component having the weak affinity for said adsorbent is formed.

7. A process for fractional separation of a plurality of components from the mixture thereof as claimed in any one of claims 1 to 5 wherein the fluid desorbent is fed into the system in the step (1).

8. A process for fractional separation of a plurality of components from the mixture thereof as claimed in claim 7: wherein said fluid desorbent is fed from the top, or upstream side, of the packed bed unit enriched with said component having the strong affinity for said adsorbent.

* * * * *